United States Patent [19]

Delarge et al.

[11] 3,991,057
[45] Nov. 9, 1976

[54] C-PIPERAZINO-PYRIDINE SULFONAMIDES

[75] Inventors: Jacques E. Delarge, Dolembreux; Leopold N. Thunus, Liege; Charles L. Lapiere, Tongeren; Andre H. Georges, Ottignies, all of Belgium

[73] Assignee: A. Christiaens Societe Anonyme, Brussels, Belgium

[22] Filed: Apr. 11, 1974

[21] Appl. No.: 459,987

Related U.S. Application Data

[63] Continuation-in-part of Ser. No. 197,139, Nov. 9, 1976, Pat. No. 3,819,639.

[30] Foreign Application Priority Data

Nov. 11, 1970 United Kingdom............... 53675/70

[52] U.S. Cl. .................... 260/268 S; 260/247.1 M; 260/268 H; 424/250
[51] Int. Cl.² .............. C07D 401/04; C07D 401/14
[58] Field of Search ... 260/268 BI, 268 H, 247.1 M, 260/268 S

[56] References Cited
UNITED STATES PATENTS

| | | | |
|---|---|---|---|
| 3,674,794 | 7/1972 | Mizzoni et al. | 260/294.8 F |
| 3,819,639 | 6/1974 | Delarge et al. | 260/294.8 F |
| 3,904,636 | 9/1975 | Delarge et al. | 260/294.8 F |

OTHER PUBLICATIONS

Bonati, et al., Chemical Abstracts, vol. 56, p. 13237, (1962).

Delarge, et al., Chemical Abstracts, vol. 77, 88325h, (1972).

Primary Examiner—Nicholas S. Rizzo
Assistant Examiner—Jose Tovar
Attorney, Agent, or Firm—Sughrue, Rothwell, Mion, Zinn & Macpeak

[57] ABSTRACT

This invention relates to compounds of the formula:

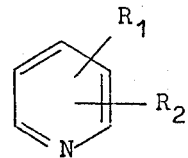

wherein $R_1$ in the 3- or 5-position is preferably a substituted sulfonamido or a carboxamido group whereas $R_2$ in the 2-, 4- or 6-position is preferably an alkyl- or hydroxyalkyl-piperazinyl group.

Said compounds may be used as anti-inflammatory and cardiovascular agents.

4 Claims, No Drawings

C-PIPERAZINO-PYRIDINE SULFONAMIDES

CROSS-RELATED APPLICATION

This invention is a continuation-in-part of our earlier application Ser. No. 197,139 filed oon Nov. 9, 1971, now U.S. Pat. No. 3,819,639.

BACKGROUND OF THE INVENTION

The present invention relates to new derivatives of pyridine having valuable pharmacological properties.

According to the present invention, there are provided compounds of formula:

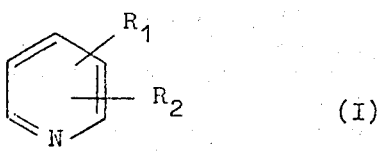

wherein $R_1$ in the 3- or 5-position of the pyridine nucleus represents a sulfonic acid group, the esters and salts thereof, a primary, secondary or tertiary sulfonamido or sulfamyl group which may be substituted, a group of formula

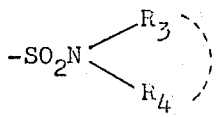

in which $R_3$ and $R_4$ form together with the nitrogen atom to which they are attached a heterocyclic ring which may contain another hetero-atom and may also be substituted, a cyano, a carboxy group, the esters and salts thereof, a primary, secondary or tertiary carboxamido or carbamyl group when $R_2$ in the 2-, 4- or 6-position represents a piperazinyl group which may be substituted as well as the pharmaceutically acceptable acid addition salts of the compounds of formula I.

A process for preparing said compounds of formula I comprises reacting a compound of formula:

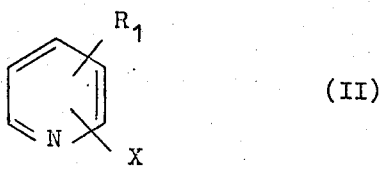

(wherein $R_1$ in the 3- or 5-position is as defined hereabove and X in the 2- or 4-position represents a halogen group) with piperazine or substituted piperazine.

In said process, whenever there is obtained a compound of formula I wherein $R_1$ represents a primary or secondary sulfonamido or carboxamido group, said compound may be acylated and whenever there is obtained a compound of formula I wherein $R_1$ represents a cyano group, said compound may be hydrolyzed to give a compound of formula I wherein $R_1$ is either carbamyl or carboxy depending on the extent of hydrolysis.

The compounds of this invention may be converted, where possible, into their acid addition salts, preferably hydrochlorides, by conventional methods.

In general formula I, $R_1$ advantageously represents a sulfonic acid or sulfonate, sulfonamido or sulfamyl, mono- and di- lower alkylsulfonamido, arylsulfonamido which latter may be substituted with one or two lower alkyl, halogeno, nitro or trifluoromethyl groups, $R_1$ may also represent a morpholino sulfone, lower alkylpiperazinylsulfone piperidinosulfone and pyrrolidinosulphone group, a cyano, carboxy, carboxylate, carboxamido or carbamyl, mono- and di- lower alkylcarboxamido, whereas $R_2$ represents a lower alkylpiperazinyl group.

Among the compounds of formulae I, II and III and their acid addition salts, prepared according to the present invention, the following are preferred on account of their especially favourable pharmacological properties:

2-(4'-methyl-1'-piperazinyl)-pyridine-3-sulfonamide
2-(4'-methyl-1'-piperazinyl)-pyridine-3-methylsulfonamide
2-(4'-methyl-1'-piperazinyl)-pyridine-3-dimethylsulfonamide
2-(4'-methyl-1'-piperazinyl)-pyridine-3-ethylsulfonamide
2-(4'-methyl-1'-piperazinyl)-pyridine-3-diethylsulfonamide dihydrochloride
2-(4'-methyl-1'-piperazinyl)-pyridine-3-isopropylsulfonamide
2-(4'-methyl-1'-piperazinyl)-pyridine-3-(4'-methyl-1'-piperazinyl)-sulfone dihydrochloride
2-(4'-methyl-1'-piperazinyl)-pyridine-5-sulfonic acid
2-(4'-methyl-1'-piperazinyl)-pyridine-5-sulfonamide
2-(4'-methyl-1'-piperazinyl)-pyridine-5-methylsulfonamide
2-(4'-methyl-1'-piperazinyl)-pyridine-5-dimethylsulfonamide
2-(4'-methyl-1'-piperazinyl)-pyridine-5-ethylsulfonamide
2-(4'-methyl-1'-piperazinyl)-pyridine-5-diethylsulfonamide
2-(4'-methyl-1'-piperazinyl)-pyridine-5-isopropylsulfonamide
2-(4'-methyl-1'-piperazinyl)-3-cyano-pyridine hydrochloride
2-(4'-methyl-1'-piperazinyl)-nicotinic acid
2-(4'-methyl-1'-piperazinyl)-pyridine-3-diethylcarboxamide and the hydrochloride thereof
2-(4'-methyl-1'-piperazinyl)-pyridine-5-diethylcarboxamide and the hydrochloride thereof.

Other interesting compounds are listed in Examples 19–48.

Among the acid addition salts of the compounds of formula I, the hydrochlorides are preferred.

The compounds of this invention have interesting anti-inflammatory, anti-pyretic and cardiovascular properties.

The anti-inflammatory properties are determined as follows:

The compounds to be tested are given as freshly prepared solutions or suspensions by oral route one hour before injecting the paw with carrageenan, a known inflammatory agent.

The inflammatory agent either in aqueous solution or suspension is then injected into the plantar tissue of the right hind paw of each rat, the left paw remaining untreated and serving as control. Each animal receives for example 0.05 ml of an aqueous solution containing 1 % of carrageenan and 0.9 % of sodium chloride.

4 hours after injection, the importance of swelling is determined by plethysmography and is expressed as a percent of the volume of the control paw.

The anti-inflammatory effect expressed as a percent of inhibition is obtained by comparison between rats treated with the anti-inflammatory agent and a control group of rats.

The results of the test for anti-inflammatory activity are given in table I.

TABLE 1

| Ref. n° | Compound of Example | Acute oedema induced by carrageenan % of inhibition |
|---|---|---|
| LT 99 | 4 | 50.0 |
| 100 | 5 | 44.0 |
| 128 | 14 | 63.2 |
| 133 | 11 | 42.4 |
| 137 | 19 | 51.2 |
| 139 | 21 | 44.4 |
| 141 | 22 | 40.0 |
| 150 | 27 | 32.0 |
| 155 | 32 | 44.8 |
| 174 | 25 | 28.8 |
| 290 | 23 | 48.8 |
| 333 | 38 | 60.8 |
| 334 | 39 | 55.2 |
| 335 | 40 | 60.0 |
| | Phenylbutazone | 41 |
| | Methiazinic acid | 46 |
| | Acetosalicylic acid | 0 |
| | Flufenamic acid | 34 |
| | Niflumic acid | 32 |

N.B.
100 mg/kg of anti-inflammatory agent are administered by oral route.

Some compounds of this invention also have interesting cardiovascular properties so that they may be used as cerebral, coronary and peripheral vasodilators and hypotension-inducing agents, whereby the hypotension activity may occur primarily or secondarily with respect to the peripheral vasodilatation.

These cardiovascular properties have been found as follows:

After administration of the compound at the hereafter-indicated doses, the following parameters are measured on the test animal: the electrocardiogram, the left ventricular pressure, the amplified telediastolic pressure, the derivative of the ventricular pressure with respect to time (dp/dt), the aortic pressure, the average and pulsatile blood flow of the left carotid and femoral artery.

LT 333 — Compound of Example 38: slight and breaf (5 min) activity on the carotid and femoral flow rates at the dose of 2 mg/kg. Similar but stronger and longer action (10 min) at doses of 4 mg/kg and 8 mg/kg, where an increase of 100 % of the average flow rates is noticed.

LT 149 — Compound of Example 33: slight increase of the average carotid flow rate at 2 mg/kg for 5 min. A dose of 4 mg/kg increases the carotid flow rate by 300 % within two minutes and the flow rate remains high when compared to control values, for 10 min. At the same dose, a 200 % increase of the femoral flow rate is observed which however falls down to the starting values within 2 min. after injection.

LT 164 — Compound of Example 29: At 2 mg/kg, moderate increase (80 % maximum) of short duration (less than 5 min.) of the femoral flow rate. At 4 mg/kg, moderate increase of the carotid (120 % maximum) and femoral (80 % maximum) flow rates for 10 minutes with slight reflex modification of the pressures. At 10 mg/kg, identical phenomena occur which are however stronger and of longer duration, the increase of the carotid flow rate reaches 300 %.

LT 155 — Compound of Example 32: a dose of 2 mg/kg causes the fall of cardiac and peripheral pressures from 150 mm of Hg to 75 mm of Hg within 45 seconds, followed by a slow and progressive recovery (reaching 135 mm of Hg after 5 minutes). Moderate increase of the carotid flow rate (60 % maximum). A dose of 4 mg/kg produces a moderate hypotension (from 135 mm of Hg to 75 mm of Hg) during more than 20 minutes. The return to the starting values (130 mm of Hg) is not effected until after 70 minutes.

LT 335 — Compound of Example 40: at 2 mg/kg, short (less than 5 min.) and strong increase of the carotid (300 % maximum) and femoral (50 % maximum) flow rates without variation of the cardiac and peripheral pressures. At 4 mg/kg, moderate fall of the blood pressure (from 150 mm of Hg to 90 mm of Hg) for 3 minutes followed by a quick return to the starting values. A moderate increase of the carotid flow rate remains after return of the pressure rates to normal conditions.

LT 334 — Compound of Example 39: at 2 mg/kg, sharp fall of the ventricular and aortic pressures (from 130 mm of Hg to 90 mm of Hg) followed by a quick return to the starting values (less than 3 min.). Slight increase of the carotid flow rate (75 %). A dose of 4 mg/kg causes a sharp fall of the same pressures (from 130 mm of Hg to 40 mm of Hg) for 2 minutes followed by a slow and progressive return to the starting values in 30 minutes. A moderate increase (50 %) of the peripheral flow rates is associated therewith.

LT 147 — Compound of Example 28: at 2 mg/kg, increase of the carotid (150 % max.) and femoral (100 % max.) flow rates for more than 5 minutes, together with a moderate and within 2 minutes reversible lowering of the ventricular and aortic pressures (from 160 mm of Hg to 100 mg of Hg). The same phenomena occur at 4 mg/kg but the lowering of pressure is sharper (from 160 mm of Hg to 70 mm of Hg) and the return to the starting values occurs progressively in 40 minutes. At 8 mg/kg, identical phenomena are observed, the pressures come back to their starting value after 50 minutes.

LT 226 — Compound of Example 48: at 2 mg/kg, moderate (100 %) but short (5 min.) increase of the carotid and femoral flow rates. A dose of 4 mg/kg causes a stronger and longer (10 min.) increase of these flow rates with a temporary and moderate fall of the ventricular and aortic pressures. Identical phenomena are observed after administration of a dose of 8 mg/kg.

According to a further feature of the present invention, we thus provide pharmaceutical compositions comprising as active ingredient, at least one compound according to the present invention, together with a pharmaceutical carrier or excipient. The compositions are generally intended for peroral rectal or parenteral administration and also for external use. Pharmaceutical compositions for oral administration may, for example, be in the form of dosage units such as tablets, dragees or capsules in which at least one of the compounds according to the invention is mixed with a solid pharmaceutical carrier or excipient.

The compositions according to the present invention can also be used in the form of liquid preparations for oral administration especially syrups, elixirs, aqueous dispersions or solutions.

The compositions according to the present invention can also be in the form of solutions for parenteral administration. Solutions or suspensions for injections can be prepared by using, for example, distilled water in which at least one compound employed as active ingredient is dissolved or suspended, if desired, in the presence of a solubilizing agent.

The compositions according to the present invention may also be formulated for rectal administration, for example, the active ingredient in a suppository base.

The anti-inflammatory compositions according to this invention may also be applied for external use, for example, the active ingredient in an ointment base.

The compounds employed as active ingredients in the compositions according to the invention can be administered in varying doses depending on the particular compound being used, the condition of the patient, and the route of administration.

In general, however, the compounds can be administered orally or rectally in doses of from 50 to 1000 mg to be taken one to four times per day, or parenterally in a single dose of 20 to 500 mg per day.

DETAILED DESCRIPTION OF THE INVENTION

EXAMPLE 1

Preparation of
2-(4'-methyl-1'-piperazinyl)-pyridine-3-sulfonamide.

The starting material 2-chloropyridine-3-sulfonamide is forst prepared as follows:

Method a: The following mixture is heated for 30 minutes at 130°–140° C: 10 g of 2-chloropyridine-3-sulfonic acid, 15 g of $PCl_5$ and a little $OPCl_3$.

The phosphorus oxychloride is distilled off in vacuo and the residue is extracted with 250 ml of anhydrous benzene. A stream of gaseous ammonia is passed or bubbled through the solution first for 30 minutes in the cold state and then for 1.5 hour with reflux heating. Upon cooling, a precipitate is formed. The latter is collected, dried and completely extracted with absolute ethanol. Evaporation of the ethanol leaves a residue which is dried and crushed and then extracted with ether to give the desired 2-chloropyridine-3-sulfonamide. Yield: 70–80 %.

Method b: Alternately, after distillation of the $OPCl_3$, the residue instead of being extracted with benzene, is poured onto 200 g of crushed ice. The mixture is stirred vigorously and 200 ml of ether are added after a few minutes. Vigorous stirring is continued and at the same time, the reaction mixture is neutralized with dry $NaHCO_3$. The mixture is extracted two times with 300 ml of ether. The ethereal solution is dried and the solvent evaporated in vacuo. The residue is extracted with 30 ml of acetone. The new solution is poured little by little and under vigorous stirring into 200 ml of concentrated ammonia. After 0.5 hour, the solution is evaporated under reduced pressure to a little volume. The desired 2-chloropyridine-3-sulfonamide crystallizes. Yield: 70–80 %. The desired product may be recrystallized from a mixture of benzene and ethanol, m.p.: 187°–188° C.

Elementary analysis:
% Calculated : C, 31.17 ; H, 2.62 ; N, 14.54 ; S, 16.64 ; Cl, 18.40. % Found : C, 31.06 ; H, 2.32 ; N, 14.89 ; S, 16.21 ; Cl 18.81.

Using 2-chloropyridine-3-sulfonamide prepared as described above, the desired end product 2-(4'-methyl-1'-piperazinyl)-pyridine-3-sulfonamide is now prepared as follows:

The following mixture is placed into a 100 ml flask: 10 g of 2-chloropyridine-3-sulfonamide, from 30 to 40 ml of toluene and 10 ml of 1-methylpiperazine. Said mixture is heated to boiling and refluxed for 4 hours. The reaction mixture is evaporated, added with water, rendered alkaline with NaOH and purified with active carbon. After filtration, the solution is brought to pH 7–8 by addition of HCl. The desired sulfonamide crystallizes, is filtered and dried. Yield: 60 %; m.p. 129°–130° C.

Elementary analysis:
% Calculated : C, 46.87; H, 6.25; N, 21.87; S, 12.50.
% Found : C, 46.75; H, 6.25; N, 21.71; S, 12.44.

EXAMPLE 2

Preparation of
2-(4'-methyl-1'-piperazinyl)-pyridine-3-methylsulfonamide 2-chloropyridine-3-methylsulfonamide is first prepared as in Example 1, method b, except that a 40 % aqueous solution of methylamine is used instead of the solution of $NH_3$. Yield: 60–70 %; m.p. 83.5° C.

Elementary analysis:
% Calculated : C, 34.87; H, 3.39; N, 13.56; S, 15.5; Cl 17.19. % Found : C, 34.61; H, 3.47; N, 13.42; S, 15.61; Cl, 17.12.

The desired piperazinylsulfonamide is now prepared as follows: the following mixture is placed into a 100 ml flask: 10 g of 2-chloropyridine-3-methylsulfonamide, 30 to 40 ml of toluene and 10 ml of 1-methylpiperazine. Said mixture is refluxed for 4 hours. The reaction mixture is evaporated under reduced pressure. The residue is taken up with water, rendered strongly alkaline with NaOH and extracted with $CHCl_3$. The extracts are dehydrated, evaporated under reduced pressure to give an oily residue which is extracted with petroleum benzine (b.p. 50°–75° C). Th precipitate obtained is filtered off, washed and recrystallized from petroleum benzine (b.p. 50°–75° C). Yield: 60–70 %; m.p. 83.5° – 85° C.

Elementary analysis:
% Calculated : C, 48.89; H, 6.67; N, 20.74; S 11.85.
% Found : C, 48.67; H, 6.65; N, 20.56; S, 11.91.

EXAMPLE 3

Preparation of
2-(4'-methyl-1'-piperazinyl)-pyridine-3dimethylsulfonamide 2-chloropyridine-3-dimethylsulfonamide is first prepared as in Example 1, method b, except that a 25–30 % aqueous solution of dimethylamine is used instead of the solution of $NH_3$. Yield: 60–70 %; m.p. 39.5° – 40.5° C.

Elementary analysis:
% Calculated : C, 38.09; H, 4.08; N, 12.70; S, 14.51; Cl, 16.10. % Found : C, 37.94; H, 4.19; N, 12.61; S, 14.37; Cl, 16.06.

The desired piperazinylsulfonamide is now prepared by the method of Example 2 using 2-chloropyridine-3-dimethylsulfonamide as starting material. Yield: 60–70 %. m.p. 78°–79° C.

Elementary analysis:

% Calculated : C, 50.70; H, 7.04; N, 19.71; S, 11.26.
% Found : C, 50.49; H, 7.26; N, 19.56; S, 11.08.

EXAMPLE 4

Preparation of 2-(4'-methyl-1'-piperazinyl)-pyridine-3-ethylsulfonamide 2-chloropyridine-3-ethylsulfonamide is first prepared as in Example 1, method b, except that a 30 % alcoholic solution of ethylamine is used instead of the $NH_3$ solution. Yield: 70–80 %; m.p. 83.5° – 85° C.

Elementary analysis:
% Calculated : C, 38.09; H, 4.08; N, 12.70; S, 14.51; Cl, 16.10. % Found : C, 37.87; H, 4.12; N, 12.65; S, 14.66; Cl, 16.03.

The desired piperazinylsulfonamide is then prepared by the method of Example 2 using 2-chloropyridine-3-ethylsulfonamide as starting material. Yield: 70%; m.p. 93°–94.5° C.

Elementary analysis: % Calculated : 50.70; H, 7.04; N, 19.71; S, 11.26. % Found : C, 50.74; H, 7.14; N, 19.57; S, 11.17.

EXAMPLE 5

Preparation of 2-(4'-methyl-1'-piperazinyl)-pyridine-3-diethylsulfonamide dihydrochloride 2-chloropyridine-3-diethylsulfonamide is first prepared as in Example 1, method b, using diethylamine (30 % aqueous solution) instead of ammonia. After 0.5 hour, the aqueous solution consisting of the reaction mixture is evaporated, neutralized with $NaHCO_3$ if necessary and extracted with $CH_2Cl_2$. The latter is evaporated under reduced pressure. The oily residue is distilled and the desired product passes at 143°–145° C under 0.1 mm of Hg and crystallizes in the receptor container. Yield: 60 %; m.p. 46°–47° C.

Elementary analysis:
% Calculated : C, 43.46; H, 5.23; N, 11.27; S, 12.87; Cl, 14.29. % Found : C, 43.24; H, 5.39; N, 11.16; S, 12.71; Cl, 14.21.

The desired piperazinylsulfonamide is then prepared by the method of Example 2 using 2-chloropyridine-3-diethylsulfonamide as starting material. The product instead of being precipitated with petroleum ether (b.p. 50°–75° C) is extracted with acetone and precipitated as a dihydrochloride by passage of gaseous HCl through the acetone solution. Yield: 60 %; m.p. 161°–163° C.

Elementary analysis:
% Calculated : C, 43.64; H, 6.75; N, 14.54; S 8.31; Cl, 20.11. % Found : C, 43.51; H, 6.91; N, 14.45; S, 8.10; Cl, 19.88.

EXAMPLE 6

Preparation of 2-(4'-methyl-1'-piperazinyl)-pyridine-3-isopropylsulfonamide 2-chloropyridine-3-isopropylsulfonamide is first prepared as in Example 1, method b, using a 30 % aqueous solution of isopropylamine instead of aqueous ammonia.

Yield: 60–70 %; m.p. 116°–118° C.
Elementary analysis:

% Calculated: C, 40.94; H, 4.68; N, 11.99; S, 13.70; Cl, 15.20. % Found: C, 40.87; H, 4.96; N, 11.84; S, 13.61; Cl, 15.12.

The desired piperazinylsulfonamide is prepared by the method of Example 2 using 2-chloropyridine-3-isopropylsulfonamide as the starting material. Yield: 60–70%; m.p. 109°–110° C.

Elementary analysis:
% Calculated: C, 52.35; H, 7.38; N, 18.79; S, 10.74. % Found: C, 52.54; H, 7.56; N, 18.62; S, 10.88.

EXAMPLE 7

Preparation of 2-(4'-methyl-1'-piperazinyl)-pyridine-3-(4'-methyl-1'-piperazinyl)-sulfone dihydrochloride The method of Example 1, method b, is applied for reacting 2-chloropyridine-3-sulfonic acid with $PCl_5$ and $OPCl_3$. However, the 2-chloropyridine-3-sulfochloride thus obtained in an acetonic solution, instead of being poured into an ammonia solution, is poured into a toluenic solution of 1-methylpiperazine. After reaction in the cold state, the mixture is refluxed for 4 hours. The desired sulfonamide is isolated in the form of the dihydrochloride thereof by applying the method described in Example 5. Yield: about 50%; m.p. 275°–277° C.

Elementary analysis:
% Calculated: C, 43.68; H, 6.55; N, 16.99; S, 7.77; Cl, 17.23. % Found: C, 43.15; H, 6.78; N, 16.72; S, 7.58; Cl, 17.16.

EXAMPLE 8

Preparation of 2-(4'-methyl-1'-piperazinyl)-pyridine-5-sulfonamide

The following mixture is placed into a 100 ml flask: 10 g of 2-chloropyridine-5-sulfonamide and 15 g of 1-methylpiperazine hydrochloride. The temperature is raised slowly up to 80° C. At the moment said temperature is reached, the reaction mass is melted and enters into reaction with spontaneous raise of the temperature. The reaction mixture is then heated to 150° C and maintained at said temperature for 15 minutes. After cooling, the reaction mass is dissolved in water rendered alkaline with soda. The pH is then adjusted to 8. The desired sulfonamide precipitates. The precipitate is collected, washed with cold water and dried. Yield: 60%; m.p. 199.5°–201° C.

Elementary analysis:
% Calculated: C, 46.87; H, 6.25; N, 21.87; S, 12.50. % Found: C, 46.65; H, 6.47; N, 21.74; S, 12.63.

EXAMPLE 9

Preparation of 2-(4'-methyl-1'-piperazinyl)-pyridine-5-methylsulfonamide

The method of Example 8 is applied using this time 2-chloropyridine-5-methylsulfonamide as starting material. The desired product is however isolated as follows: the aqueous alkaline solution is extracted with $CHCl_3$. The $CHCl_3$ solution is evaporated under reduced pressure and the desired product is precipitated by means of petroleum ether (b.p. 50°–75° C). Yield: 60%.

Elementary analysis:
% Calculated: C, 48.89; H, 6.67; N, 20.74; S, 11.85. % Found: C, 48.71; H, 6.83; N, 20.61; S, 11.73.

EXAMPLE 10

Preparation of 2-(4'-methyl-1'-piperazinyl)-pyridine-5-dimethylsulfonamide

The method of Example 9 is applied, using this time 2-chloropyridine-5-dimethylsulfonamide as starting material. The isolation method is also as in Example 9. Yield: 60%.

Elementary analysis:
% Calculated: C, 50.70; H, 7.04; N, 19.71; S, 11.26.
% Found: C, 50.61; H, 7.18; N, 19.62; S, 11.13.

EXAMPLE 11

Preparation of 2-(4'-methyl-1'-piperazinyl)-pyridine-5-ethylsulfonamide.

The method of Example 2 is applied using however 2-chloropyridine-5-ethylsulfonamide as starting material. Yield: 60–70%; m.p. 133.5°–135° C.

Elementary analysis:
% Calculated: C, 50.70; H, 7.04; N, 19.71; S, 11.26.
% Found: C, 50.52; H, 7.30; N, 19.83; S, 11.32.

EXAMPLE 12

Preparation of 2-(4'-methyl-1'-piperazinyl)-pyridine-5-diethylsulfonamide

The method of Example 2 is applied using however 2-chloropyridine-5-diethylsulfonamide. Yield: 60–70%; m.p. 105°–106° C.

Elementary analysis:
% Calculated: C, 53.84; H, 7.69; N, 17.95; S, 10.26.
% Found: C, 53.66; H, 7.84; N, 17.82; S, 10.11.

EXAMPLE 13

Preparation of 2-(4'-methyl-1'-piperazinyl)-pyridine-5-isopropylsulfonamide

The method of Example 2 is applied except that 2-chloropyridine-5-isopropylsulfonamide is used as starting material. Yield: 60–70%; m.p. 132°–133.5° C.

Elementary analysis:
% Calculated: C, 52.35; H, 7.38; N, 18.79; 10.74. % Found: C, 52.15; H, 7.51; N, 18.61; S, 10.89.

EXAMPLE 14

Preparation of 2-(4'-methyl-1'-piperazinyl)-3-cyanopyridine hydrochloride

The method of Example 5 is applied except that 2-chloro-3-cyanopyridine is used as starting material. Before precipitating the hydrochloride, the solution of extraction is evaporated under reduced pressure to remove the excess of 1-methylpiperazine. The residue is then extracted with acetone and the method is further applied as in Example 5. Yield: 60%; m.p. 221°–222.5° C.

Elementary analysis:
% Calculated: C, 55.46; H, 6.30; N, 23.48. % Found: C, 55.30; H, 6.53; N, 23.31.

EXAMPLE 15

Preparation of 2-(4'-methyl-1'-piperazinyl)-nicotinic acid

A solution of 10% NaOH is added to 10 g of 2-(4'-methyl-1'-piperazinyl)-3-cyanopyridine hydrochloride and refluxed for 6 hours. The mixture is allowed to cool and brought to pH 8 by means of concentrated HCl. After evaporation to dryness under means of concentrated HCl. After evaporation to dryness under reduced pressure, the residue is extracted with a mixture of equal parts of absolute alcohol and benzene. The liquid of extraction is then evaporated under reduced pressure until the desired nicotinic acid crystallizes as white crystals. Yield: 60%; m.p.: 269° C.

Elementary analysis:
% Calculated: C, 59.73; H, 6.78; N 19.00. % Found: C, 59.61; H, 6.97; N, 18.84.

EXAMPLE 16

Preparation of 2-(4'-methyl-1'-piperazinyl)-pyridine-3-diethylcarboxamide and the hydrochloride thereof 2-chloropyridine-3-diethylcarboxamide is first prepared by either of the following methods:

Method 1:

The following mixture is placed into a 100 ml flask provided with two necks: 10 g of diethyl-nicotinamide-1-oxide and 50 ml of $OPCl_3$. The mixture is heated to 120° C and 30 g of $PCl_5$ are added little by little. The temperature is maintained at 120° C for 1.5 hour. After cooling, the $OPCl_3$ is evaporated under reduced pressure. The oily residue is poured onto ice and neutralized with $NaHCO_3$. It is extracted with $CHCl_3$. The chloroformic solution is evaporated under reduced pressure and the residue is distilled off in vacuo. The desired 2-chloro-diethylcarboxamide passes at 150°–155° C under 0.4–0.5 mm of Hg. Yield: 60%.

Method 2

The following mixture is refluxed for 3 hours: 10 g of 2-chloro-nicotinic acid and 80 ml of thionyl chloride. The reaction mixture is evaporated to dryness, extracted with 100 ml of hexane, again evaporated to dryness and the same operation is repeated two further times. The residue is extracted with 50 ml of acetone and the solution thus obtained is poured dropwise and with stirring into a mixture of 20 ml of diethylamine and 80 ml of benzene. After addition, the reaction mixture is evaporated under reduced pressure. The residue is added with water and sodium hydroxide and then extracted with $CHCl_3$. The chloroformic solution is dried on dry $Na_2SO_4$ and evaporated under reduced pressure. The residue is distilled in vacuo. The desired 2-chloro-diethylcarboxamide passes at 150°–155° C under 0.4–0.5 mm of Hg.

Elementary analysis:
% Calculated: C, 56.47; H, 6.12; N, 13.18; Cl, 16.70.
% Found: C, 56.34; H, 6.23; N, 13.29; Cl, 16.69.

The desired 2-(4'-methyl-1'-piperazinyl)-pyridine-3-diethylcarboxamide is then prepared as follows: 10 g of 2-chloropyridine-3-diethylcarboxamide, 30–40 ml of toluene and 10 g of 1-methyl-piperazine are placed in a 100 ml flask. The reaction mixture is refluxed for 4 hours. A solution is thus obtained and is evaporated under reduced pressure. The residue is taken with $H_2O$ and NaOH and is then extracted with CHCl₃. The chloroformic extracts are evaporated under reduced pressure and the residue thereof is distilled in vacuo. The product passes at about 175° C under 0.4–0.5 mm of Hg. It is taken or extracted with anhydrous acetone and dry gaseous HCl is bubbled through the acetonic solution. The desired product precipitates as its hydrochloride. Yield: 70%; m.p. 225°–226.5° C.

Elementary analysis:
% Calculated: C, 57.58; H, 8.00; N, 17.98. % Found: C, 57.79; H, 8.09; N, 17.82.

EXAMPLE 17

Preparation of 2-(4'-methyl-1'-piperazinyl)-pyridine-5-sulfonic acid 10 g of 2 -chloropyridine-5-sulfonic acid, 15 ml of 1-methylpiperazine and 0.5 g of copper powder are placed into a 100 ml flask. The mixture is heated at 140°–150° C for 5 hours. It is then taken with methanol, the copper is filtered off, the solution is evaporated to dryness and the residue is taken with absolute ethanol to recrystallize the desired product. Yield: 70%; m.p. 322°–324° C.

Elementary analysis:
% Calculated: C, 46.69; H, 5.83; N, 16.34; S, 12.45. % Found: C, 46.51; H, 6.01; N, 16.21; S, 12.39.

EXAMPLE 18

Preparation of 2-(4'-methyl-1'-piperazinyl)-pyridine-5-diethylcarboxamide and the hydrochloride thereof The method of Example 16 is applied, using 2-chloropyridine-5-diethylcarboxamide as starting material and refluxing the reaction mixture for 8 hours.

Upon distillation, the desired product passes at 220°–230° C under 1.5 mm of Hg.

The hydrochloride thereof is precipitated in the same way as in Example 16.

EXAMPLES 19–22

These examples illustrate the preparation of the following products:

2-(4'-methyl-1'-piperazinyl)-pyridine-3-methylcarboxamide (Example 19)

2-(4'-methyl-1'-piperazinyl)-pyridine-3-dimethylcarboxamide (Example 20)

2-(4'-methyl-1'-piperazinyl)-pyridine-3-ethylcarboxamide (Example 21)

2-(4'-methyl-1'-piperazinyl)-pyridine-3-isopropylcarboxamide (Example 22).

These products are prepared by the following general method:

A mixture of 10 g of starting chlorinated compound of formula II, 30–40 ml of toluene and 10 g of N-methylpiperazine is heated and boiled under reflux conditions for 4 hours. After cooling, the solution is evaporated under reduced pressure to obtain an oil. 20 ml water and 20 ml NaOH are added and the mixture is extracted with chloroform. The extraction solution is then dried and distilled.

Particulars of the compounds are set out in the following table.

TABLE II

Starting product of formula II

| $R_1$ | Compound of Example obtained | Boiling point °C/mm | Yield % | Melting point °C |
|---|---|---|---|---|
| CONHCH₃ | 19[1] | 184–187°/0.5 | 60 | 95–97 |
| CON(CH₃)₂ | 20[2] | 185–190°/1 | 60 | 235 |
| CONHC₂H₅ | 21[1×3] | 185–190°/0.8 | 60 | 69 |
| CONHCH(CH₃)₂ | 22[1] | 187–192°/0.5 | 70 | 81 |

[1] crystallizes at rest
[2] precipitated as hydrochloride from a solution in acetone by means of gaseous hydrochloride
[3] distilled under nitrogen blanket

EXAMPLES 23–27

These examples illustrate the preparation of the following products:

2-(4'-methyl-1'-piperazinyl)-5-cyanopyridine (Example 23)

2-(4'-methyl-1'-piperazinyl)-5-methylcarboxamide (Example 24)

2-(4'-methyl-1'-piperazinyl)-5-dimethylcarboxamide (Example 25)

2-(4'-methyl-1'-piperazinyl)-5-ethylcarboxamide (Example 26)

2-(4'-methyl-1'-piperazinyl)-5-isopropylcarboxamide (Example 27)

These products are prepared by the following general method:

A mixture of 10 g of chlorinated starting compound of formula II, 30 to 40 ml of toluene and 10 g of N-methylpiperazine is heated and boiled under reflux conditions during 4 hours. After cooling, the solution thus obtained is evaporated under reduced pressure. 20 ml water and 20 ml NaOH (10%) are added and the resulting mixture is extracted with CHCl₃. The extraction solution is dried and then evaporated under reduced pressure. The residue is taken up with petroleum ether and stirred until it crystallizes. The solid product is filtered and then crystallized from petroleum ether.

Particulars of the compounds are set out in the following table:

TABLE III

Starting compounds of formula II

| $R_1$ | Product of Example obtained | Melting point °C | Yield % | Analysis C | H | N |
|---|---|---|---|---|---|---|
| CN | 23 | 61–62.5 | 75 | 65.34[1] | 6.93 | 27.72 |
| | | | | 65.05[2] | 7.12 | 27.61 |
| CONHCH₃ | 24 | 112–113 | 60 | 61.54 | 7.69 | 23.93 |
| | | | | 61.48 | 7.71 | 23.75 |
| CON(CH₃)₂ | 25 | 86.5–87.5 | 60 | 62.90 | 8.06 | 22.58 |

TABLE III-continued

Starting compounds of formula II

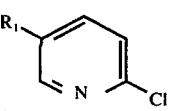

| R₁ | Product of Example obtained | Melting point °C | Yield % | Analysis | | |
|---|---|---|---|---|---|---|
| CONHC$_2$H$_5$ | 26 | 85–97 | 70 | 62.70<br>62.90 | 8.25<br>8.06 | 22.65<br>22.58 |
| CONHC$_3$H$_7$iso | 27 | 145–146 | 70 | 62.75<br>64.12<br>64.03 | 8.15<br>8.40<br>8.39 | 22.75<br>21.37<br>21.50 |

[1] calculated
[2] found

EXAMPLES 28–40

The starting compounds of formula II are first prepared by the following method:

A mixture of 10 g 4-hydroxy-pyridine-3-sulfonic acid, 40 g of PCl$_5$ and 40 ml of OPCl$_3$ is heated at 125°–130° C during 2 hours. After cooling, the not reacted OPCl$_3$ is evaporated under reduced pressure. The residue is taken up with 100 ml of ether and poured into 100 g of ice. The mixture thus obtained is stirred vigorously until the excess of PCl$_5$ and OPCl$_3$, if any, is decomposed. The acidity is neutralized by means of NaHCO$_3$ and the solution is extracted 3 times with 100 ml of ether. The ether solution is dried by means of anhydrous sodium sulfate and is evaporated under reduced pressure. The remaining sulfochloride is then dissolved in 30-50 ml of dioxane and poured drop by drop, with constant stirring, into 200 ml of a cold aqueous solution of the appropriate amine. After addition of the sulfochloride, one waits 10 further minutes and then one concentrates, if necessary, the solution under reduced pressure. The crystalline product is recovered by filtration, washed and recrystallized from the suitable solvent. In some instances, the product is extracted with CHCl$_3$ and distilled under vacuum.

Particulars of the starting compounds of formula II thus obtained are given in the following table.

TABLE IV

Compounds of formula II

| —R | Yield % | Melting point °C | Recrystallization solvent | Used for Example N° |
|---|---|---|---|---|
| —NH$_2$ | 70 | 175.5–177 | a | 28 |
| —NHCH$_3$ | 70[1] | 187.5–189 | a | 29 |
| —N(CH$_3$)$_2$ | 70[1] | 95 | b (155–160° /0.4 mm) | 30 |
| —NHC$_2$H$_5$ | 75 | 139–140 | a | 31 |
| —N(C$_2$H$_5$)$_2$ | 65 | 91.5–93 | b (180° /0.5 mm) | 32 |
| —NHC$_3$H$_7$iso | 75 | 107–109 | a | 33 |
| —N⟨azetidine⟩ | 75[1] | 46.5–47.5 | c | 34 |
| —N⟨piperidine⟩ | 75[1] | 86–88 | c | 35 |
| —N⟨morpholine⟩ | 75 | 126–127.5 | c | 37 |
| —NHCH$_2$CH$_2$OCH$_3$ | 75 | 118–119 | c | 39 |

TABLE IV-continued

Compounds of formula II (structure: pyridine with Cl and SO₂R substituents)

| −R | Yield % | Melting point °C | Recrystallization solvent | Used for Example N° |
|---|---|---|---|---|
| −NHCH₂CH₂OC₂H₅ | 75 | 101.5–102.5 | c | 40 |

(1) worked at 0° C
(a) water-alcohol
(b) distilled under vacuum, then crystallized at rest
(c) petroleum ether (b.p. 100–140° C)

Using the compounds of formula II prepared as described hereabove, the following compounds of formula I are now prepared.:

4-(4'-methyl-1'-piperazinyl)-pyridine-3-sulfonamide (Example 28)
4-(4'-methyl-1'-piperazinyl)-pyridine-3-methylsulfonamide (Example 29)
4-(4'-methyl-1'-piperazinyl)-pyridine-3-dimethylsulfonamide (Example 30)
4-(4'-methyl-1'-piperazinyl)-pyridine-3-ethylsulfonamide (Example 31)
4-(4'-methyl-1'-piperazinyl)-pyridine-3-diethylsulfonamide (Example 32)
4-(4'-methyl-1'-piperazinyl)-pyridine-3-isopropylsulfonamide (Example 33)
4-(4'-methyl-1'-piperazinyl)-pyridine-3-pyrrolidinosulfone (Example 34)
4-(4'-methyl-1'-piperazinyl)-pyridine-3-piperidinosulfone (Example 35)
4-(4'-methyl-1'-piperazinyl)-pyridine-3-(4''-methyl-1''-piperazinyl)-sulfone (Example 36)
4-(4'-methyl-1'-piperazinyl)-pyridine-3-morpholinosulfone (Example 37)
4-(4'-methyl-1'-piperazinyl)-pyridine-3-(4''-methyl-1'''-piperazinyl)-ethylsulfonamide (Example 38)
4-(4'-methyl-1'-piperazinyl)-pyridine-3-methyoxyethylsulfonamide (Example 39)
4-(4'-methyl-1'-piperazinyl)-pyridine-3-ethoxyethylsulfonamide (Example 40

These compounds are prepared by the following method:

10 g of the starting chlorinated compound of formula II are placed in a flask with 30-40 ml of toluene and 15 ml of N-methylpiperazine. The mixture is heated under boiling and reflux conditions during 4 hours. After cooling, the solution is evaporated under reduced pressure. 20 ml of water and 20 ml of NaOH (10%) are added and the mixture is extracted with CHCl₃. The chloroform solution is dried and then evaporated under reduced pressure. The residue is recrystallized from the appropriate solvent.

TABLE V

| Compound of Example | Yield % | Melting point °C | Recrystallization solvent |
|---|---|---|---|
| 28 | 70 | 185 | a |
| 29 | 70 | 180–181.5 | b |
| 30 | 70 | 116.5–118 | a |
| 31 | 75 | 132.5–134 | a |
| 32 | 65 | 76.5–78 | a |
| 33 | 80 | 116 | a |
| 34 | 75 | 111–112 | c |
| 35 | 80 | 112–113 | c |
| 36 | 70 | 287–288.5 | d |
| 37 | 80 | 127–128 | c |
| 38 | 65 | 109.5–111 | c |
| 39 | 80 | 118–119.5 | c |
| 40 | 80 | 90–91.5 | c | a benzene - petroleum ether
b benzene-methanol
c petroleum ether (100–140° C)
d precipitation of the hydrochloride from a solution in acetone.

EXAMPLES 41–47

These examples illustrate the preparation of the following compounds:

4-(4'-hydroxyethyl-1'-piperazinyl)-pyridine-3-sulfonamide (Example 41)
4-(4'hydroxyethyl-1'piperazinyl)-pyridine-3-ethylsulfonamide (Example 42)
4-(4'-hydroxyethyl-1'-piperazinyl)-pyridine-3-diethylsulfonamide (Example 43)
4-(4'-hydroxyethyl-1'-piperazinyl)-pyridine-3-isopropylsulfonamide (Example 44)
4-(4'hydroxyethyl-1'-piperazinyl)-pyridine-3-piperidinosulfone (Example 45)
4-(4'-hydroxyethyl-1'-piperazinyl)-pyridine-3-morpholinosulfone (Example 46)
4-(4'-hydroxyethyl-1'-piperazinyl)-pyridine-3-pyrrolidinosulfone (Example 47).

The above-cited compounds are prepared by the same method as the compounds of Examples 28–40.

Particulars of said compounds are set out in the following table:

TABLE VI

| Compound of Example | Yield % | Melting point °C | Recrystallization solvent |
|---|---|---|---|
| 41 | 60 | 222.5 | a |
| 42 | 80 | 119–120 | b |
| 43 | 60 | — (285–290°/0.1 mm) | c |
| 44 | 75 | 93 | b |
| 45 | 75 | 116–117.5 | b |
| 46 | 75 | 82.5–84 | d |
| 47 | 75 | 95–96.5 | b | a water-alcohol
b petroleum ether - b.p. 100–140° C
c distilled under vacuum
benzene-hexane

EXAMPLE 48

Preparation of 4-(4'-methyl-1'-piperazinyl)-pyridine-3-dimethylaminomethinesulfonamide (Formula I: $R_1 = SO_2N=CH-N(CH_3)_2$).

5 g of 4-(4'-methyl-1'-piperazinyl)-pyridine-3-sulfonamide are dissolved in 10 ml of dimethylformamide (heated to 80° C if necessary). 7 ml of $SOCl_2$ are added slowly, while maintaining the temperature below 80° C. The temperature is maintained at 80° C during 15–20 minutes. The mixture is poured into 100 ml of water. The solution is alkalinized with $NH_4OH$ to pH 8–9, extracted with $CHCl_3$. The chloroform solution thus obtained is dried and evaporated under reduced pressure. The residue is recrystallized from petroleum ether - benzene. Yield: 65%. Melting point: 137°–138° C.

Examples of compositions for use according to this invention are now given hereinafter:

EXAMPLE 49

| Dragees: | |
|---|---|
| Core: | |
| Compound of formula I | 50.0 mg |
| Colloidal silica | 5.0 mg |
| Lactose | 42.5 mg |
| Polyvidone | 3.5 mg |
| Glycerol | 0.5 mg |
| Maize starch | 8.0 mg |
| Talc | 10.0 mg |
| Magnesium stearate | 0.5 mg |
| Coating: | |
| Gum lac | 2.0 mg |
| Gum arabic | 5.4 mg |
| New-Coccine | 0.1 mg |
| Talc | 13.0 mg |
| Colloidal silica | 9.5 mg |
| Saccharose | 50.0 mg |
| | for one degree |

EXAMPLE 50

| Tablets: | |
|---|---|
| Core: | |
| Compound of formula I | 200.0 mg |
| Colloidal silica | 17.0 mg |
| Stearic acid | 4.0 mg |
| Gelatine | 4.0 mg |
| Glycerol | 1.6 mg |
| Maize starch | 52.0 mg |
| Magnesium stearate | 1.4 mg |
| | for one tablet |

EXAMPLE 51

| Capsulses: | |
|---|---|
| Compound of formula I | 100.0 mg |
| Lactose | 120.0 mg |
| Rice starch | 30.0 mg |
| Maize starch | 30.0 mg |
| Magnesium stearate | 5.0 mg |
| Gelatine } envelope | 78.0 mg |
| Tartrazine | 0.2 mg |
| | for one capsule |

EXAMPLE 52

| Suppositories: | |
|---|---|
| Compound of formula I | 300 mg |
| Witepsol H 12 mass ( ) | 600 mg |
| | for one suppository |

( ) a mixture of triglycerides and partial glycerides of saturated fatty acids ($C_{12}$—$C_{18}$) originating from plants, furnished by Dynamit Nobel AG, Koln-Mulheim, Western Germany.

EXAMPLE 53

| Vials: | |
|---|---|
| Compound of formula I | 20.0 mg |
| Natrium chloride | 85.0 mg |
| Distilled water to form | 10.0 ml |
| | for one vial |

What we claim is:
1. A pyridine compound of the formula:

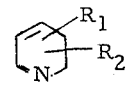

wherein $R_1$ in the 3- or 5-position of the pyridine nucleus represents a group of the formula

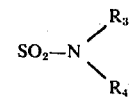

in which $R_3$ and $R_4$ are hydrogen, alkyl of 1 to 3 carbon atoms, methoxyethyl, ethoxyethyl or together with the nitrogen atom form pyrrolidino, piperidino, morpholino or 4-methylpiperazino, provided $R_3$ and $R_4$ are methoxyethyl or ethoxyethyl only when one of them is hydrogen; and $R_2$ in the 2-, 4-or 6-position represents 4-methylpiperazino or 4-hydroxyethylpiperazino, and the pharmaceutically acceptable acid addition salts thereof.

2. A compound according to claim 1, wherein $R_1$ in the 3-position represents ethylsulfonamido or diethylsulfonamido, when $R_2$ in the 2-position represents N-methyl-piperazino.

3. A compound according to claim 1, wherein $R_1$ in the 5-position represents ethylsulfonamido whereas $R_2$ in the 2-position represents N-methyl-piperazino.

4. A compound according to claim 1, wherein $R_1$ in the 3-position represents sulfonamido, methylsulfonamido, diethylsulfonamido, isopropylsulfonamido, N-methylpiperazinylsulfone, methoxyethylsulfonamido or ethoxyethylsulfonamido, while $R_2$ in the 4-position represents N-methylpiperazino.

* * * * *